US010703652B2

(12) United States Patent
Ikeda et al.

(10) Patent No.: US 10,703,652 B2
(45) Date of Patent: *Jul. 7, 2020

(54) FORWARD OSMOSIS PROCESS

(71) Applicant: FUJIFILM Corporation, Minato-ku, Tokyo (JP)

(72) Inventors: Morihito Ikeda, Ashigarakami-gun (JP); Kimiaki Miyamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 119 days.

This patent is subject to a terminal disclaimer.

(21) Appl. No.: 15/963,753

(22) Filed: Apr. 26, 2018

(65) Prior Publication Data

US 2018/0257959 A1 Sep. 13, 2018

Related U.S. Application Data

(60) Division of application No. 15/085,197, filed on Mar. 30, 2016, now Pat. No. 10,087,090, which is a
(Continued)

(30) Foreign Application Priority Data

Sep. 29, 2010 (JP) .................. 2010-218911

(51) Int. Cl.
*B01D 61/00* (2006.01)
*C02F 1/44* (2006.01)
(Continued)

(52) U.S. Cl.
CPC ............ *C02F 1/445* (2013.01); *B01D 61/002* (2013.01); *B01D 61/005* (2013.01);
(Continued)

(58) Field of Classification Search
CPC .... B01D 61/00; B01D 61/002; B01D 61/005; B01D 63/00; B01D 65/00; B01D 2311/04;
(Continued)

(56) References Cited

U.S. PATENT DOCUMENTS 3,171,799 A 3/1965 Batchelder
6,391,205 B1 5/2002 McGinnis
(Continued)

FOREIGN PATENT DOCUMENTS

WO 2007/146094 A2 12/2007
WO 2007/147013 A1 12/2007
WO 2011/097727 A1 8/2011

OTHER PUBLICATIONS

Michael H. Hiatt, "Determination of Henry's Law Constants Using Internal Standards with Benchmark Values", Mar. 2013, Journal of Chemical Engineering, vol. 58, pp. 902-908. (Year: 2013).*
(Continued)

*Primary Examiner* — Joseph W Drodge
(74) *Attorney, Agent, or Firm* — Sughrue Mion, PLLC

(57) ABSTRACT

A forward osmosis apparatus includes a diluting component for bringing a feed solution and a draw solution containing a cation source and an anion source in an ionized state into contact through a semi-permeable membrane and diluting the draw solution with water separated from the feed solution by means of the semi-permeable membrane; a separator for separating the draw solution that has been diluted by the diluting component into the cation source and anion source and into water; and a dissolving apparatus, returning the cation source and the anion source that have been separated by the separator to, and dissolving the cation source and anion source in, the draw solution that has been diluted, wherein the molecular weight of the cation source in an uncharged state is 31 or greater and the Henry's law constant
(Continued)

of each of the anion source and cation source is 1.0×104 (Pa/mol·fraction) or greater in a standard state.

18 Claims, 3 Drawing Sheets

Related U.S. Application Data division of application No. 13/827,047, filed on Mar. 14, 2013, now Pat. No. 9,630,861, which is a continuation of application No. PCT/JP2011/072261, filed on Sep. 28, 2011.

(51) Int. Cl.
| | |
|---|---|
| C07C 211/00 | (2006.01) |
| C01B 32/60 | (2017.01) |
| C02F 103/08 | (2006.01) |
| C02F 1/02 | (2006.01) |
| C02F 1/16 | (2006.01) |
| C02F 1/20 | (2006.01) |

(52) U.S. Cl.
CPC ...... *B01D 2311/2626* (2013.01); *C01B 32/60* (2017.08); *C02F 1/02* (2013.01); *C02F 1/16* (2013.01); *C02F 1/20* (2013.01); *C02F 1/447* (2013.01); *C02F 2103/08* (2013.01); *C02F 2209/005* (2013.01); *C02F 2209/02* (2013.01); *C02F 2303/16* (2013.01); *C07C 211/00* (2013.01); *Y02A 20/131* (2018.01); *Y02W 10/37* (2015.05)

(58) Field of Classification Search
CPC .......... B01D 2311/10; B01D 2311/103; B01D 2311/106; B01D 2311/12; B01D 2311/25; B01D 2311/2626; C02F 1/44; C02F 1/445; C02F 1/447; C02F 1/16; C02F 1/20; C02F 1/02; C02F 2209/02; C02F 2209/005; C02F 2103/08; C02F 2303/16; C02F 2311/2626; C02F 2315/16; Y02A 20/131; Y02W 10/37; C01B 32/60; C07C 211/00; C07C 211/01
USPC ....... 210/637, 639, 644, 649, 650, 652, 177, 210/198.1, 195.1, 805; 252/181
See application file for complete search history.

(56) References Cited

U.S. PATENT DOCUMENTS

| | | | |
|---|---|---|---|
| 7,790,944 B2 | 9/2010 | O'Ham | |
| 8,216,474 B2 | 7/2012 | Cath et al. | |
| 9,630,861 B2* | 4/2017 | Ikeda | B01D 61/002 |
| 10,087,089 B2* | 10/2018 | Ikeda | B01D 61/002 |
| 10,087,090 B2* | 10/2018 | Ikeda | B01D 61/002 |
| 2005/0145568 A1 | 7/2005 | Mc Ginnis | |
| 2006/0011544 A1 | 1/2006 | Sharma et al. | |
| 2006/0144789 A1 | 7/2006 | Cath et al. | |
| 2006/0237366 A1* | 10/2006 | Al-Mayahi | B01D 61/002 |
| | | | 210/644 |
| 2009/0308727 A1 | 12/2009 | Kirts | |
| 2010/0155329 A1 | 6/2010 | Iyer | |
| 2010/0155331 A1 | 6/2010 | Bryan et al. | |
| 2010/0183903 A1 | 7/2010 | McGinnis et al. | |
| 2010/0224561 A1 | 9/2010 | Marcin | |
| 2011/0155666 A1 | 6/2011 | Prakash et al. | |
| 2012/0273417 A1 | 11/2012 | McGinnis | |
| 2018/0250634 A1* | 9/2018 | Harris | B01D 61/005 |

OTHER PUBLICATIONS

Rolf Sander, "Compilation of Henry's law constants, version 3.99", Nov. 2014, Atmospheric Chemistry and Physics Discussions, vol. 14, pp. 29615-30521. (Year: 2014).*
Rolf Sander, "Compilation of Henry's Law Constants for Inorganic and Organic Species of Potential Importance in Environmental Chemistry", Apr. 1999, Air Chemistry Department, Max-Planck Institute of Chemistry, Mainz, Germany, Version 3. (Year: 1999).*
Communication dated Dec. 11, 2014, issued by the State Intellectual Property Office of the People's Republic of China in counterpart Chinese Application No. 201180046282.3.
International Search Report for PCT/JP2011/072261 dated Dec. 20, 2011.
Rolf Sander, "Compilation of Henry's Law Constants for Inorganic and Organic Species of Potential Importance in Environmental Chemistry", Apr. 8, 1999, http://www.mpch-mainz.mpg.de/~sander/res/henry.html, 107 pgs.
Office Action dated Jul. 1, 2014 in Chinese Application No. 201180046282.3.
Written Opinion of the International Searching Authority dated Dec. 20, 2011 in PCT/JP2011/072261.
McCutcheon, Jeffrey R. et al., "A novel ammonia-carbon dioxide forward (direct) osmosis desalination process", Desalination, vol. 174, No. 1, Apr. 1, 2005.
International Preliminary Report on Patentability dated Apr. 2, 2013 in PCT/JP2011/072261.
Search Report dated Feb. 21, 2014 in European Application No. 11 82 9222.
Communication dated Dec. 29, 2016, from the United States Patent and Trademark Office in U.S. Appl. No. 13/827,047.
Office Action dated Dec. 19, 2017 in co-pending U.S. Appl. No. 15/040,327.

\* cited by examiner

Correlation of molecular weight of cation source and leakage

Correlation of Henry's constant × molecular weight and leakage

FORWARD OSMOSIS PROCESS

The present application is a Divisional Application of U.S. patent application Ser. No. 15/085,197, filed Mar. 30, 2016, which is a Divisional Application of U.S. application Ser. No. 13/827,047, filed Mar. 14, 2013, which is a Continuation Application of PCT/JP2011/072261, filed Sep. 28, 2011 and claims priority under 35 U.S.C. § 119 of Japanese Patent Application No. 218911/2010, filed Sep. 29, 2010, the disclosures of which are incorporated herein by reference.

The present invention relates to a forward osmosis process (FO process) and to a forward osmosis apparatus (FO apparatus) capable of conducting separation and/or concentration by this FO process.

BACKGROUND ART

Water shortages have become a serious problem in arid regions of the world and in regions of high population density. Accordingly, there is a need for desalination technology that removes salt from seawater.

Membrane processing methods are a known desalination technology. In membrane processing methods, semi-permeable membranes are generally employed. Semi-permeable membranes are known as membranes that pass only molecules and ions of a specific size or smaller. For example, they are membranes that pass the water but not the salt in seawater. When two solutions of differing solute concentrations are brought into contact through a semi-permeable membrane, osmotic pressure is generated between the two solutions. The solvent of the solution on the side of low solute concentration, that is, the side of low osmotic pressure, passes to the side of high solute concentration, that is, the side of high osmotic pressure. This phenomenon of osmosis theoretically continues until the stage where the osmotic pressure differential decreases to zero. For example, when seawater and water are brought into contact through a semi-permeable membrane, the water tends to pass through to the seawater side and create a state of equilibrium.

The reverse osmosis process (RO process) and forward osmosis process (FO process) are known membrane processing methods utilizing such semi-permeable membranes.

The RO process is an osmotic technique whereby low-molecular-weight components such as water are caused to move from the side of high osmotic pressure back through to the side of low osmotic pressure. A high pressure exceeding the osmotic pressure differential of the two solutions is applied to the side of high osmotic pressure in the RO process to bring about such reverse osmosis. For example, when separating water from seawater, seawater and water are brought into contact through a semi-permeable membrane, and pressure exceeding the osmotic pressure differential between the seawater and the water, normally pressure greatly exceeding this osmotic pressure differential, is applied to the seawater side to cause the water in the seawater to pass through to the water side.

By contrast, the FO process is a process whereby a solution with a high osmotic pressure draw (draw solution) is employed to artificially generate an osmotic pressure differential between the two solutions and cause the water to migrate, as disclosed in Patent References 1 and 2. Specifically, a starting solution in the form of a feed solution (feed solution) and a draw solution of higher osmotic pressure than the feed solution are brought into contact through a semi-permeable membrane. When that is done, the osmotic pressure differential between the two solutions causes the water in the feed solution to pass through to the draw solution side. Subsequently, the solute component in the draw solution is volatilized and recovered to separate out the water in the feed solution. There are also cases where the concentrated feed solution is separated out.

An example of a case of separating water from seawater will be described next based on FIG. 1.

FIG. 1 shows an example of a seawater processing apparatus utilizing the FO process. The solid-line arrows show the flow of seawater or water 11 separated from seawater, and the dotted lines show the flow of draw solution or draw solution solute 12, respectively. Initially, seawater 11 and draw solution 12 come into contact through a semi-permeable membrane 13. The water in seawater 11 passes through semi-permeable membrane 13 to the draw solution 12 side. Then, in stripping column 14, the solute component of the draw solution is volatilized from the draw solution that has been diluted by the water of the seawater, thereby separating out the water 16 and solute component 15 of the draw solution. The solute component 15 of the draw solution is dissolved in draw solution that has been diluted in a gas absorber 17, and reused as draw solution 12. Numeral 18 denotes a pressure gauge.

Gasifying and separating the solute component of the draw solution in stripping column 14 requires high volatility. The solute component of the draw solution must also have a high degree of solubility so that it will dissolve in the diluted draw solution. Further, the solute component of the draw solution must naturally not pass through the semi-permeable membrane. When these requirements are not met, there will be problems in the FO apparatus or FO process in that the rate of permeation through the semi-permeable membrane by water from the feed solution will be poor; the solute in the draw solution will end up leaking through the semi-permeable membrane and migrating to the feed solution side, speeding up the rate; and the quantity of draw solution solute (stripping performance) remaining in the water obtained by volatilizing the solute component from the draw solution that has been diluted with water from the feed solution will be large.

Examples employing draw solutions in the form of solutions of ammonia ions and carbon dioxide, ammonia ion solutions, sulfur dioxide solutions, and the like are known (Patent References 2 and 3). However, none fully combining the above high volatility, high solubility, and property of not passing through semi-permeable membranes has yet been obtained.

PRIOR ART REFERENCES

Patent References

[Patent Reference 1] U.S. Pat. No. 6,391,205
[Patent Reference 2] US Patent Application Publication 2005/0145568
[Patent Reference 3] U.S. Pat. No. 3,171,799

SUMMARY OF INVENTION

Problem to Be Solved by the Invention

Patent Reference 2 achieves high volatility while ensuring a high degree of solubility of solute components in the draw solution by using a draw solution with ammonia and carbon dioxide as solutes, thereby achieving both enhanced processing performance and enhanced stripping performance in the FO process. However, during examination, the present inventors encountered a problem in that the ammonia ended up leaking out through the semi-permeable membrane in the diluting means. That is, in the process of Patent Reference 2, it was necessary to replenish large amounts of ammonia in the FO apparatus. In Patent Reference 3, the rate of leakage through the semi-permeable membrane was reduced by employing sulfurous acid as a solvate component of the draw solution. However, it was impossible to use anything but a solvate of low volatility to achieve high solubility in the draw solution, precluding adequate stripping performance.

The present invention has for its object to maintain a high passage rate through a semi-permeable membrane by water from a feed solution in an FO apparatus and in an FO process, control the migration of draw solution solute to the feed solution side due to leakage through the semi-permeable membrane, and reduce the quantity of draw solution solute remaining in the water obtained by volatizing the solute component from the draw solution that has been diluted with feed solution water (enhance the stripping performance).

Means of Solving the Problem

The present inventors conducted extensive research based on these conditions, resulting the discovery that the above-stated problem could be solved by employing a draw solution containing an anion source and a cation source such that the cation source had a molecular weight of 31 or higher in an uncharged state and the cation source and the anion source each had a Henry's law constant of $1.0 \times 10^4$ (Pa/mol·fraction) or higher in a standard state.

Generally, the lower the Henry's law constant, the greater the tendency to hydrate and the larger the hydration radius are thought to be (reference: *Journal of Chemical & Engineering Data*, 53 (2008), 2873-2877, expanded equations (4), (5), and (6), $\ln K_{aw} = \Delta G_{hyd}/RT$, where $K_{aw}$=dimensionless Henry's law constant, $\Delta G_{hyd}$=hydration free energy (with the tendency to hydrate increasing with the magnitude of the negative value, R is Avogadro's constant, and T is absolute temperature). Further, the greater the hydration radius, the slower the leakage of solute through the semi-permeable membrane is thought to be (reference: *Desalination*, 144 (2002), 387-392, FIG. 2(*b*), page 390, line 7, left column to line 8, right column; reference: *Journal of Membrane Science*, 74 (1992), 05-103, FIGS. 4 and 5, page 98, line 34, left column to page 101, line 9, left column). This naturally shows that the greater the level of hydration of a material, the less prone it is to volatilize in water (the lower the Henry's law constant), indicating that it is difficult to achieve both a tendency not to leak through semi-permeable membranes and a tendency to volatilize. Accordingly, it was thought that it would be extremely difficult to solve the above-stated problem by adjusting the components of the draw solution. Surprisingly, however, extensive research by the present inventors resulted in the discovery that the problem could be solved by employing draw solution solute components in the form of a cation source and an anion source of greater than or equal to specified molecular weights and having specified Henry's law constants.

Specifically, the problem of the present invention was solved by the following means.

<1> A forward osmosis apparatus, comprising a diluting means for bringing a feed solution and a draw solution comprising a cation source and an anion source in an ionized state into contact through a semi-permeable membrane and diluting the draw solution with water separated from the feed solution by means of the semi-permeable membrane;

a separating means for separating the draw solution that has been diluted by the diluting means into the cation source and anion source and into water; and a dissolving means, returning the cation source and the anion source that have been separated by the separating means to, and dissolving the cation source and anion source in, the draw solution that has been diluted;

wherein the cation source in an uncharged state has a molecular weight of 31 or greater, and each of the anion source and cation source has a Henry's law constant of $1.0 \times 10^4$ (Pa/mol·fraction) or greater in a standard state.

<2> The forward osmosis apparatus according to <1>, wherein the anion source has an acid dissociation constant (pKa) of 6.0 to 7.0 as an uncharged material in a standard state.

<3> The forward osmosis apparatus according to <1> or <2>, wherein the cation source has a base dissolution constant (pKb) of 2.0 to 4.5 as an uncharged material in a standard state.

<4> The forward osmosis apparatus according to any one of <1> to <3>, wherein the cation source and/or anion source has a boiling point of less than 100° C. at 1 atm as an uncharged material.

<5> The forward osmosis apparatus according to any one of <1> to <4>, wherein the cation source has a base dissolution constant (pKb) of 4.0 to 4.5 as an uncharged material in a standard state.

<6> The forward osmosis apparatus according to any one of <1> to <5>, wherein the cation source has a Henry's law constant of $1.0 \times 10^5$ (Pa/mol·fraction) or greater in a standard state.

<7> The forward osmosis apparatus according to any one of <1> to <6>, wherein the cation source has a Henry's law constant of $1.0 \times 10^5$ (Pa/mol·fraction) or greater in a standard state.

<8> The forward osmosis apparatus according to any one of <1> to <7>, wherein each of the anion source and cation source in the draw solution has a concentration immediately prior to being contacted with the semi-permeable membrane of 2.4 mol or more per kilogram of water.

<9> The forward osmosis apparatus according to any one of <1> to <8>, wherein the anions are carbonic acid anions and/or hydrogen carbonate atoms.

<10> The forward osmosis apparatus according to any one of <1> to <9>, wherein the molar ratio of the anion source and cation source is from 1:1 to 1:2.

<11> The forward osmosis apparatus according to any one of <1> to <10>, wherein the cation source is an amine compound.

<12> The forward osmosis apparatus according to any one of <1> to <11>, wherein the cation source is one or more members selected from the group consisting of trimethyl amine, dimethyl ethyl amine, isopropyl amine, dimethyl amine, and diethyl amine.

<13> The forward osmosis apparatus according to any one of <1> to <12>, wherein the cation source and anion source have a Henry's law constant of each of $1.00 \times 10^5$ (Pa/mol·fraction) or greater, and the cation source has a molecular weight of a range of from 45 to 74.

<14> The forward osmosis apparatus according to any one of <1> to <13>, wherein the cation source is trimethyl amine or dimethyl ethyl amine, and the anion source is carbon dioxide.

<15> The forward osmosis apparatus according to any one of <1> to <14>, wherein the diluted draw solution is separated into the cation source and anion source and into water by heating to a temperature not exceeding 90° C.
<16> The forward osmosis apparatus according to any one of <1> to <15>, wherein the draw solution that is introduced by the diluting means has a temperature of ±5° C. of the feed solution introduced by the diluting means.
<17> The forward osmosis apparatus according to any one of <1> to <16>, which comprises a heat exchanger that warms the diluted draw solution using, as a heat source, at least one among the water, cation source, and anion source obtained by the separating means.
<18> The forward osmosis apparatus according to any one of <1> to <17>, which comprises a heat exchanger that cools at least one among the cation source and anion source obtained by the apparatus of the dissolving means or the separating means using the feed solution prior to dilution as a cooling source.
<19> The forward osmosis apparatus according to any one of <1> to <18>, wherein the difference between the maximum temperature of the separating means and the minimum temperature of the dissolving means is less than 35° C.
<20> The forward osmosis apparatus according to any one of <1> to <19>, wherein the forward osmosis apparatus is a water purification apparatus that separates the draw solution diluted by the diluting means into a cation source and anion source and into water, and recovers the water component as a target product.
<21> The forward osmosis apparatus according to <20>, wherein the feed solution is seawater.
<22> The forward osmosis apparatus according to any one of <1> to <21>, wherein the forward osmosis apparatus is a concentrating device that recovers the feed solution that has been concentrated after bringing the feed solution and draw solution into contact through the semi-permeable membrane as a target product.
<23> A draw solution for a forward osmosis process, comprising an anion source and a cation source, wherein the cation source has a molecular weight of 31 or greater in an uncharged state, and each of the anion source and cation source in water has a Henry's law constant of $1.0 \times 10^4$ (Pa/mol·fraction) or greater in a standard state.
<24> The draw solution for a forward osmosis process according to <23>, wherein the acid dissolution constant (pKa) of the anion source as an uncharged material in a standard state is 6.0 to 7.0.
<25> The draw solution for a forward osmosis apparatus according to <23> or <24>, wherein the anion source has an acid dissolution constant (pKa) of 6.0 to 7.0 as an uncharged material in a standard state.
<26> The draw solution for a forward osmosis apparatus according to any one of <23> to <25>, wherein the cation source in water has a Henry's law constant of $3.0 \times 10^4$ (Pa/mol·fraction) or greater in a standard state.
<27> The draw solution for a forward osmosis apparatus according to any one of <23> to <26>, wherein each of the anion source and the cation source has a concentration of 2.4 mol or more per kilogram of water.
<28> The draw solution for a forward osmosis apparatus according to any one of <23> to <27>, wherein the anions are carbonic acid ions and/or hydrogen carbonate ions, and the cation source is one or more members selected from the group consisting of trimethyl amine, dimethyl ethyl amine, isopropyl amine, dimethyl amine, and diethyl amine.

<29> A forward osmosis process, comprising:
bringing a feed solution and a draw solution comprising a dissolved cation source and an anion source into contact through a semi-permeable membrane and diluting the draw solution with a liquid separated from the feed solution by the semi-permeable membrane;
separating the diluted draw solution into the cation source and anion source and into water; and
returning the separated cation source and anion source to, and dissolving the separated cation source and anion source in, the diluted draw solution;
wherein the molecular weight of the cation source in an uncharged state is 31 or greater and the Henry's law constant in water in a standard state of each of the anion source and the cation source is $1.0 \times 10^4$ (Pa/mol·fraction) or greater.

Effect of the Invention

The FO apparatus and FO process of the present invention make it possible to maintain a high permeation rate, inhibit leakage of draw solution solute through the semi-permeable membrane and migration to the feed solution side, and reduce the quantity of draw solution solute remaining in water obtained by volatilizing solute components from the draw solution that has been diluted with water from the feed solution (enhance stripping performance). As a result, it becomes possible to utilize the FO apparatus and implement the FO process without replenishing draw solution solute components.

MODES OF CARRYING OUT THE INVENTION

Figure 1:
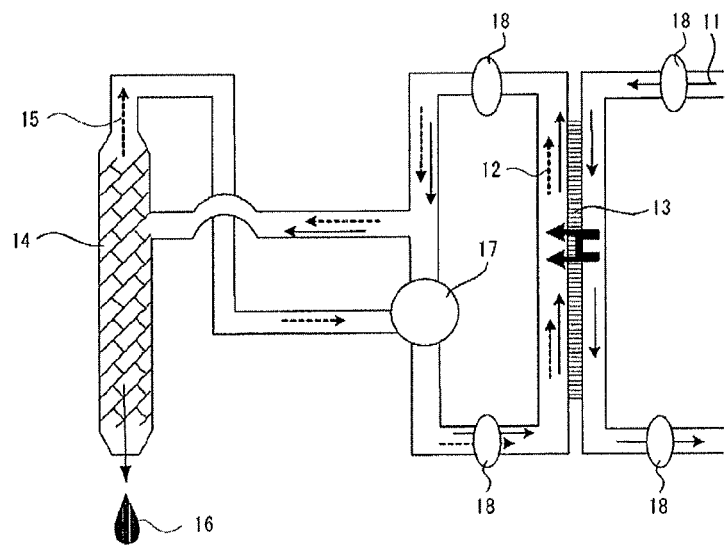
FIG. 1 is an example showing the configuration of a conventional FO apparatus.

The contents of the present invention are described in detail below. In the present description, numeric values preceding and succeeding the word "to" are employed to mean the maximum and minimum values, inclusive, of a range.

In the present description, the term "anion source" refers to a substance that generates anions when dissolved in water, and the term "cation source" refers to a substance that produces cations when dissolved in water. Accordingly, the anion source and cation source are normally uncharged materials. In the present invention, the term "standard state" means 25° C. and $10^5$ Pa (about 1 atmosphere).

The FO apparatus of the present invention comprises a diluting means for bringing a feed solution and a draw solution comprising a cation source and an anion source in an ionized state into contact through a semi-permeable membrane and diluting the draw solution with water separated from the feed solution by means of the semi-permeable membrane; a separating means for separating the draw solution that has been diluted by the diluting means into the cation source and anion source and into water; and a dissolving means, returning the cation source and the anion source that have been separated by the separating means to, and dissolving the cation source and anion source in, the draw solution that has been diluted; wherein the molecular weight of the cation source in an uncharged state is 31 or greater and the Henry's law constant of each of the anion source and cation source is $1.0 \times 10^4$ (Pa/mol·fraction) or greater in a standard state. The present invention will be described in detail below.

The FO apparatus of the present invention refers to an apparatus that conducts separation, concentration, filtration, and the like by an FO process. That is, it is not specifically prescribed so long as it comprises a method of artificially generating an osmotic pressure differential between two solutions with a draw solution of high osmotic pressure to cause water to migrate. For example, the case where an osmotic pressure differential is applied and pressure is applied to force feed a liquid is also covered by the FO process of the present invention. Accordingly, in the FO apparatus of the present invention, the target product that is ultimately recovered can be the water that is separated on the draw solution side or the liquid that is concentrated on the feed solution side.

When recovering the water that is separated on the draw solution side as the target product, the FO apparatus of the present invention is desirably a water purification device. The feed solution that is employed is not specifically limited and can be suitably selected based on the objective. Examples are seawater, brackish water, river water, water obtained from locations in the natural world such as lakes, swamps, and ponds, industrial waste water discharged by factories and various industrial facilities, common waste water discharged by households and common facilities, and microorganism culture solutions at water treatment facilities. Of these, seawater is preferred due to its ready availability in stable, large quantities and the need for purification.

When recovering the concentrated feed solution as the target product, the FO apparatus of the present invention is desirably a concentrating apparatus. In this case, examples of such feed solutions are concentrated fruit juices and vegetable juices.

The FO apparatus of the present invention normally comprises a diluting means, separating means, and dissolving means, as well as other means as needed. The FO process of the present invention comprises diluting, separating, and dissolving, and is carried out by the FO apparatus of the present invention.

<The Diluting Means>

The diluting means is a process where the feed solution and the draw solution are brought into contact through a semi-permeable membrane and the semi-permeable membrane dilutes the draw solution with water that is separated from the feed solution. This process can be conducted at 15 to 40° C., for example. When the draw solution that is introduced by the diluting means is warmed by the feed solution, the solute in the draw solution gasifies and potentially forms bubbles. Conversely, when cooled, the solute in the draw solution potentially precipitates. Thus, the temperature of the draw solution that is introduced is desirably ±5° C. that of the feed solution that is introduced by the diluting means. Further, the liquid feed pressure of the feed solution can be such that driving is conducted at a low pressure different from that in RO, such as $1 \times 10^4$ Pa to $5 \times 10^5$ Pa.

The semi-permeable membrane is not specifically limited in terms of its material, shape, size, configuration, or the like, and can be suitably selected based on the objective. For example, it can be a flat membrane, a spiral module employing a flat membrane, a hollow fiber module, or a tubular module. The feed direction of the draw solution and feed solution with respect to the surface of the membrane is not limited; feeding can be conducted antiparallel, parallel, or in a non-parallel direction such as at an angle of 90°. The thickness of the feed flow route as measured from the surface of the semi-permeable membrane is not specifically limited, and can be from 10 μm to 10 mm, by way of example. The shallower the flow route the better because the permeation efficiency of water from the feed solution through the semi-permeable membrane increases. However, clogging and the like also tend to occur, so a suitable thickness is selected.

Nor is the material of the semi-permeable membrane specifically limited other than that it be capable of separating water and solute. Examples are cellulose acetate, aromatic polyamides, aromatic polysulfones, and polybenzoimidazoles. A polyamide or cellulose acetate with a degree of acetyl group substitution of 2.50 to 2.95 is desirably selected.

The method of manufacturing the semi-permeable membrane is not specifically limited other than that separation of water and solute be possible. Examples are the non-solvent induced phase separation method (NIPS), thermally induced phase separation method (TIPS), interfacial polymerization method, and solvent evaporation method. For example, various membrane-manufacturing methods can be conducted by the methods described in experimental membrane science methods in A Compilation of Artificial Membranes (compiled by the Membrane Society of Japan), 1.2 Methods for manufacturing macromolecular membranes. When manufacturing a semi-permeable membrane by the solvent evaporation method, a thin membrane with a thickness of less than 1 μm is desirable. In that case, there is a risk of damaging the semi-permeable membrane in the course of peeling the thin membrane off the coating substrate (including film forms). Thus, the method of coating a sacrificial layer on the coating substrate in advance and peeling off one membrane for each sacrificial layer can be adopted. Here, the term "sacrificial layer" refers to a layer that spontaneously peels off or dissolves when immersed in solvent, heated, or the like.

A membrane that is employed as a RO membrane can be employed as is, or in an improved form, as the semi-permeable membrane in addition to a film manufactured as a FO membrane. However, a FO membrane in which deterioration in permeation performance has been inhibited by internal concentration polarization is desirably selected. As specific examples, the Expedition built-in membrane and the X-Pack built-in membrane, both made by Hydration Technology Innovation, can be employed.

The Feed Solution

The feed solution is not specifically limited. It can be suitably selected based on the objective. Examples are seawater, brackish water, river water, water obtained from locations in the natural world such as lakes, swamps, and ponds, industrial waste water discharged by factories and various industrial facilities, common waste water discharged by households and common facilities, microorganism culture solutions at water treatment facilities, membrane bioreactor (MBR) microorganism culture solutions, fruit juices, and vegetable juices. Of these, seawater is preferred due to its ready availability in stable, large quantities and the need for purification.

The feed solution can be subjected to various pretreatments prior to processing by the diluting means. Examples are common water treatment methods such as flocculent treatment, sedimentation treatment, and filtration treatments such as sand filtration and microfiltration. A further example is the method of dilution by prior use of the feed solution as a draw solution in another forward osmosis apparatus, such as the osmotic dilution described in the *Journal of Membrane Science*, 362 (2010), pp. 417-426. Reducing the solute concentration of the feed solution by that method can be anticipated to have effects such as enhancing the dilution rate in the forward osmosis apparatus of the present invention and greatly reducing the energy input.

The Draw Solution

The draw solution comprises solutes in the form of an anion source and a cation source each having a Henry's law constant of $1.0 \times 10^4$ (Pa/mol·fraction) or greater. The Henry's law constant is a physical property indicating the relation between the mol fraction of a substance and the saturation vapor partial pressure in a solution in which a large quantity of a solution has been dissolved in water. The greater this constant, the greater the volatility in the aqueous solution and the lower the solubility indicated. It is described in books: *Chemistry Handbook* (published by Maruzen K.K.) and *Gas Absorption, Supplemented* (published by Kagaku Kogyo K.K.); in the literature: Compilation of Henry's Law Constants for Inorganic and Organic Species of Potential Importance in Environmental Chemistry (hyperlink: http://www.mpch-mainz.mpg.de/~sander/res/henry.html); and the like. When the solute becomes charged (ions), since only the uncharged component of the solute correlates to the saturation vapor pressure, the Henry's law constant is a physical property that indicates the relation between the mol fraction of the uncharged component of the solute and the saturation vapor partial pressure. Thus, when the anion source and cation source become charged in the form of anions and cations based on the pH of the aqueous solution, the saturation vapor pressure drops, that is, the solubility increases. Since an anion source and a cation source with high Henry's law constants of $1.0 \times 10^4$ (Pa/mol fraction) or greater are employed in the present invention, solubility is low in the uncharged state. However, when the anion source and the cation source are brought together to adjust the pH, the ratio of each of the charged materials increases and their solubility increases markedly relative to the case of the solution alone.

The draw solution comprises an anion source and a cation source. Here, the anion source and the cation source are contained in the draw solution in an ionized state.

The content of the anion source and cation source in the draw solution is not specifically limited and can be suitably selected based on the objective.

In the diluting means, high concentrations are desirable from the perspective of increasing the rate of separation of water from the feed solution. For example, the total concentration of dissolved solute in the draw solution just prior to the diluting means is desirably 4.8 mol or more per kilogram of water. There is a risk of inviting deterioration of the semi-permeable membrane and the like if the pH of the solution is extremely high or low, so the pH is desirably 4 to 10. When employing carbon dioxide as the anion source, a mixing ratio that yields pH 8 or higher is desirable to increase solubility. The molar ratio of the anion source and cation source is desirably 1:1 to 1:2, preferably 1:1.2 to 1:1.7. A suitable value is selected for this ratio based on the species of anion and cation.

In the separating means, it is desirable for the diluted draw solution to be of low concentration from the perspectives of increasing separation efficiency and reducing the energy required for separation. Thus, the dilution rate in the diluting means is desirably high. However, when the osmotic pressure differential between the diluted draw solution and the feed solution decreases, the permeation rate of water through the semi-permeable membrane in the diluting means drops sharply, so a suitable concentration and dilution rate are selected.

The Cation Source

The molecular weight of the cation source in the present invention is 31 or greater in an uncharged state and the Henry's law constant in a standard state is $1.0 \times 10^4$ (Pa/mol·fraction) or greater. Employing such a cation source with the anion source makes it possible to maintain a high permeation rate of water through the semi-permeable membrane and to inhibit leakage of the solute in the draw solution through the semi-permeable membrane and migration to the feed solution side in an FO apparatus. It also reduces the amount of draw solution solute remaining in the water obtained by volatilizing the solute component from the draw solution that has been diluted with water from the feed solution (enhances stripping performance).

The molecular weight of the cation source in an uncharged state is desirably 45 to 74, preferably 45 to 62.

The Henry's law constant of the cation source in a standard state is desirably $1.0 \times 10^5$ (Pa/mol·fraction) or greater. The upper limit is not specifically set. By way of example, it can be $1.0 \times 10^7$ (Pa/mol·fraction) or lower. Setting it to within such a range makes it possible to raise the volatility in the separating means, and as a result, reduce the quantity of water that ends up unnecessarily volatilizing in the separating means. As a result, it becomes possible to keep down the energy required for separation.

When the base dissociation constant (pKb) of the cation source as an uncharged material is excessively low in the standard state, there are problems in that the volatilization decreases in the separating means, the quantity of cation source remaining in the separated water increases, and the energy required for separation increases. Conversely, when the pKb is excessively high, there are problems in that the pH in the absorber drops, the quantity of anion source dissolving decreases, and the permeation rate of water through the semi-permeable membrane decreases in the diluting means. Thus, the pKb must be suitably selected and is desirably 2.0 to 4.5, preferably 4.0 to 4.5.

Keeping the molecular weight, Henry's law constant, and pKb of the cation source within the above suitable ranges more effectively inhibits the cation source from leaking through the semi-permeable membrane and migrating to the feed solution side, raises the separation efficiency of the separating means, keeps down the energy required for separation, and raises the efficiency of the diluting means.

The boiling point of the cation source as an uncharged material at 1 atm is desirably less than 100° C., preferably not greater than 50° C. Remaining within this range inhibits the condensation during operation of gas in the cation source that has been separated in the separating means. The lower limit is not specifically set. For example, it can be −20° C. or higher.

The concentration of the cation source in the draw solution just before being brought into contact with the semi-permeable membrane is desirably 2.4 mol or more per kilogram of water, preferably 3.0 mol/kg or more. Adopting such means makes it possible to raise the permeation rate of water through the semi-permeable membrane in the diluting means. The upper limit is not specifically limited, and can normally be 8.0 mol/kg or less.

The cation source need not be specifically limited to remain within the spirit and scope of the present invention. However, it is desirably an amine compound and can be denoted by general formula (I) below.

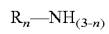
$$R_n—NH_{(3-n)} \qquad \text{General formula (I):}$$

(In general formula (I), R denotes a linear or branched aliphatic group with 1 to 4 carbon atoms and n denotes 1, 2, or 3.)

In general formula (I), R desirably denotes a methyl group with 1 carbon atom and n desirably denotes 3.

Specific examples are one or more selected from among trimethyl amine, dimethyl ethyl amine, isopropyl amine, dimethyl amine, diethyl amine, n-propyl amine, ethyl amine, n-butyl amine, isopropyl amine, isobutyl amine, t-butyl amine, pyrrolidine, methyl amine, ethyl methyl amine, methyl n-propyl amine, methyl isopropyl amine, pentyl amine, dimethyl n-propyl amine, dimethyl isopropyl amine, ethyl n-propyl amine, ethyl isopropyl amine, and diethyl methyl amine; more preferably one or more selected from among trimethyl amine, dimethyl ethyl amine, isopropyl amine, dimethyl amine, and diethyl amine; and still more preferably, trimethyl amine or dimethyl ethyl amine.

The Anion Source

The anion source in the present invention has a Henry's law constant in a standard state of $1.0 \times 10^1$ (Pa/mol·fraction) or greater. Employing such an anion source in combination with the cation source maintains a high permeation rate and inhibits the solute in the draw solution from leaking through the semi-permeable membrane and migrating to the feed solution side in a FO apparatus, as well as reducing the amount of draw solution solute remaining in the water obtained by volatilizing the solute component from the draw solution that has been diluted with feed solution water (enhancing stripping performance).

The base dissociation constant (pKb) of the anion source as an uncharged material in a standard state is desirably 2.0 to 4.5, preferably 4.0 to 4.5. Keeping it within such a range has the effects of causing preferential volatilization and separation over cations in the separating means, enhancing overall separation efficiency, and inhibiting leakage of the anion source through the semi-permeable membrane and migration to the feed solution side in the diluting means.

The boiling point of the anion source as an uncharged material at 1 atm is desirably less than 100° C., preferably not greater than 50° C., and more preferably, not greater than 0° C. Keeping it within such a range has the effects of causing preferential volatilization and separation over cations in the separating means and enhancing overall separation efficiency. The lower limit is not specifically set. However, it is normally −100° C. or higher.

The Henry's law constant of the anion source in a standard state is preferably $1.0 \times 10^7$ (Pa/mol·fraction) or greater. Keeping it within such a range has the effects of causing preferential volatilization and separation over cations in the separating means and enhancing overall separation efficiency. The upper limit is not specifically set, but is normally $1.0 \times 10^{10}$ (Pa/mol·fraction) or lower.

In the standard state, the acid dissociation constant (pKa) of the anion source as an uncharged material is desirably 6.0 to 7.0.

The concentration of the anion source in the draw solution just before being brought into contact with the semi-permeable membrane is desirably 2.4 mol or more per kilogram of water, preferably, 2.8 mol/kg or more. Employing such a means increases the permeation rate of water through the semi-permeable membrane in the diluting means. The upper limit is not specifically set, but is normally 8.0 mol/kg or less.

The anion source need not be specifically limited to remain within the spirit and scope of the present invention. Examples are carbon dioxide ($CO_2$), carbonic acid ($H_2CO_2$), and sulfur dioxide ($SO_2$). Of these, carbon dioxide ($CO_2$) is particularly desirable from the perspectives of high volatility, stability, low reactivity, and ready availability. Accordingly, a mixture of carbonic acid ions and hydrogen carbonate ions is desirable as the anions. In some cases, complex ions such as carbamate ions can be incorporated.

<The Dissolving Means>

The dissolving means returns and dissolves the volatile solutes of the draw solution that have been separated by the separating means to the draw solution that has been diluted by the diluting means. The dissolving means is not specifically limited and can be suitably selected based on the objective from among those apparatus that are commonly employed to absorb gases. For example, the apparatus, parts, conditions, and the like that are described in the book: *Gas Absorption, Supplemented* (published by Kagaku Kogyo K.K.), pp. 49 to 54, pp. 83 to 144, can be optionally employed. Specific examples are methods employing absorbers, packed columns, tray columns, spray columns, and fluid packed columns; liquid film crossflow contact methods; high-speed rotating flow methods; and methods utilizing mechanical forces. It is also possible to construct and cause the absorption of thin gas and liquid layers using microfluidic control devices such as microreactors and membrane reactors. Structures similar to the absorbers employed in heat pumps such as ammonia absorption chillers can also be employed.

The packings that are packed into packed columns can be structured packings or unstructured packings. For example, the packings described in the book: *Gas Absorption, Supplemented* (published by Kagaku Kogyo K.K.), pp. 221 to 242 can be optionally selected.

Structural parts and materials such as packings, columns, distributors, and supports are not specifically limited and can be suitably selected based on the objective. Examples are steel-based materials such as stainless steel and aluminum killed steel; nonferrous materials such as titanium and aluminum; ceramics such as glass and alumina; and materials such as carbon, synthetic polymers, and rubbers. To efficiently absorb the anion source and cation source gases in the dissolving means, the presence of a cooling function is desirable. The cooling function can of an integrated form with heat exchanging elements that run throughout the dissolving means, or in the form of one or multiple heat exchangers attached to one part of the dissolving means. From the perspective of efficient dissolution, an integrated form is desirably selected. Multiple types of gas absorbers can be employed in the dissolving means.

A low operating temperature in the dissolving means generally enhances dissolving efficiency. However, since an immense amount of cooling energy is required to get below ordinary temperature, from the perspective of the amount of energy required, a temperature of ordinary temperature or above, or from ordinary temperature to 15° C. above ordinary temperature is desirable. Here, the term "ordinary temperature" means ambient temperature.

\<The Separating Means\>

In the separating means, the volatile solute in the draw solution is separated from the draw solution that has been diluted by the diluting means and a target solution such as water or a concentrated feed solution is obtained.

The separating means need not be specifically limited to remain within the spirit and scope of the present invention. It can be suitably selected based on the objective. Examples are the stripping columns, stripping apparatus, membrane processing units, microreactors, and other microfluidic control devices commonly employed in stripping. Of these, stripping columns are preferred.

When employing a stripping column, the heating temperature is desirably not greater than 90° C., preferably not greater than 75° C. Employing such a means permits the use of a heat medium of low utility value as the energy source, thereby greatly enhancing economy. The lower limit is not specifically established, but is normally 30° C. or higher.

The method of heating in the separating means can be suitably selected so long as it permits heating of the diluted draw solution. From the perspective of economy, it is desirable to select a method of heating that utilizes waste heat of less than 100° C., not electrical heating or high-temperature heat sources of 100° C. or higher. Specifically, power plants such as thermal power plants and nuclear power plants, incineration furnaces, steel-making industry and petrochemical industry plants, sunlight collection systems employing mirrors and lenses, and the like can be selected. The selection of a power plant is desirable from the perspective of the quantity of waste heat.

The stripping column is not specifically limited and can be suitably selected based on the objective. Examples are tray columns and packed columns.

Examples of tray columns are structures described in the books *Distillation Technology* (published by Kagaku Kogyo K.K.), pp. 139 to 143 and *Chemical Engineering Explained* (published by Baifukan), pp. 141 to 142. Specific examples are bubble cap trays, valve trays, and porous sheet (sieve) trays.

The packings that are packed into packed columns can be structured packings or unstructured packings. For example, the packings described in *Chemical Engineering Explained* (published by Baifukan), pp. 155 to 157, and *Gas Absorption, Supplemented* (published by Kagaku Kogyo K.K.), pp. 221 to 242 can be optionally selected.

For example, the membrane distillation unit described in a scientific paper in the *Journal of Membrane Science*, Vol. 124, Issue 1, pp. 1 to 25 and the like can be employed as a membrane processing unit.

For example, the reactor described in the book *Techniques and Applications of Microchemical Chips* (published by Maruzen) can be employed as a microreactor.

When employing carbon dioxide as the anion source, slower reactions than in hydrocarbon-based stripping columns, such as hydration and dehydration, are involved and an extremely long time is required to achieve gas-liquid equilibrium. Thus, to get the separating means to function efficiently, it is desirable to keep the solution in the various packings and trays for longer than the recommended retention time calculated for a hydrocarbon system. Examples of common methods that can be adopted to lengthen the retention time are increasing the diameter of the stripping column, selecting a tray column, and adjusting the pore size.

\<Other Processes\>

Examples of other processes are control processes and driving processes. These are carried out by control means and driving means.

The control means is not specifically limited other than it be capable of controlling the operation of each means, and can be suitably selected based on the objective. Examples are devices such as sequencers and computers.

\<Required Energy\>

In the forward osmosis process of the present invention, relatively specific conditions such as the anion source and cation source can be selected to greatly reduce the energy required. In particular, since a low quality heat source can be employed as the energy source utilized in the forward osmosis process, great significance is achieved in manufacturing. Here, the term "low quality energy" refers to energy that cannot be used in common applications, or that affords poor efficiency. For example, for heat of less than 100° C., the electricity conversion efficiency of turbines and the like is poor, and the utility value of such heat is low. The forward osmosis process of the present invention mainly requires feed energy and heating energy in the separating means. However, since the feed pressure is low, in contrast to RO, heating energy accounts for most of the energy in the separating means. However, when the temperature in the dissolving means is lower than ordinary temperature, the cooling temperature becomes immense. Thus, it must be set to greater than or equal to ordinary temperature. Thus, to reduce the overall energy, optimal conditions must be selected for the entire system, not just the separating means.

When a thermodynamic simulation of the forward osmosis system of the present invention was simulated, reducing the quantity of water that ended up being needlessly volatilized with the anion source and cation source in the separation element was found to effectively keep down the energy in the separating means. In particular, when carbon dioxide was employed as the anion source, separation occurred with the anion source volatilizing preferentially in the initial period in the separating means. Thus, the ease with which the remaining cation source volatilized and separated was important. That is, the selection criterion for the cation source is not its volatilization energy; it is important to select cations with a high Henry's law constant and a high pKb. In the dissolving means, it is necessary to efficiently dissolve the carbon dioxide, but as set forth above, an immense amount of cooling energy becomes necessary when the temperature in the dissolving means is made excessively low. Thus, a range of from ordinary temperature to ordinary temperature plus 15° C. is desirable. To enhance the dissolution efficiency of carbon dioxide, a high pH is desirable in the draw solution. Thus, the pkb of the cation source is desirably low. The fact that the pKb that is required in the cation source runs counter to what is needed in the separating means and dissolving means in this manner indicates that a suitable range will be present. Specifically, from the perspective of the energy required, a pKb of 3.2 to 4.5 and a Henry's law constant of $1.0 \times 10^5$ (Pa/mol·fraction) or greater are desirable, and a pKb of 4.0 to 4.5 and a Henry's law constant of $3.0 \times 10^5$ (Pa/mol·fraction) or greater are preferred in the cation source. More specifically, trimethyl amine or dimethyl ethyl amine is desirably selected, for example.

In addition to the above, the techniques described in U.S. Pat. No. 6,391,205, US Patent Application Publication 2005/0145568, and International Publication No. WO2007/146094 can be adopted in the present invention to an extent that does not depart from the spirit or scope of the present invention.

Embodiments

The present invention is described more specifically below through embodiments. The materials, quantities employed, ratios, processing contents, processing procedures and the like that are indicated in the embodiments below can be suitably modified within departing from the spirit or scope of the present invention. Accordingly, the scope of the present invention is not limited by the specific examples given below.

In the present embodiments, the following substances were employed as the cation source and anion source.

The Henry's law constant is a value based on the Compilation of Henry's Law Constants for Inorganic and Organic Species of Potential Importance in Environmental Chemistry (hyperlink: http://www.mpch-mainz.mpg.de/~sander/res/henry.html). For substances for which multiple values were listed, extreme values were eliminated and the average value was employed. It is denoted in units of Pa/mol·fraction. The molecular weight is the molecular weight of the respective compound in an uncharged state. The pKa and pKb are the usual values based on the literature, such as the *Chemical Handbook, Basic Edition*, ed. by the Chemical Society of Japan, Maruzen. The boiling point is a value based on 1 atm.

Figure 3:
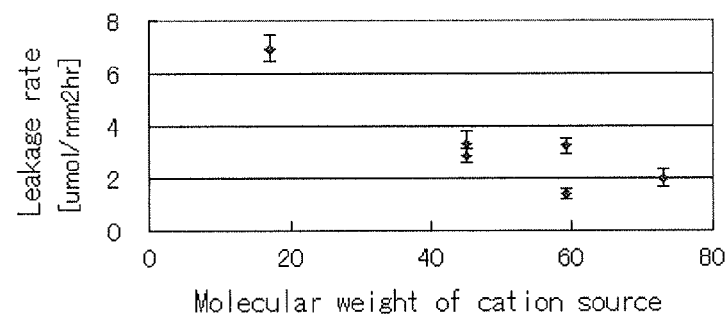
FIG. 3 is a graph of the correlation between the molecular weight of the cation source and leakage.
Figure 4:
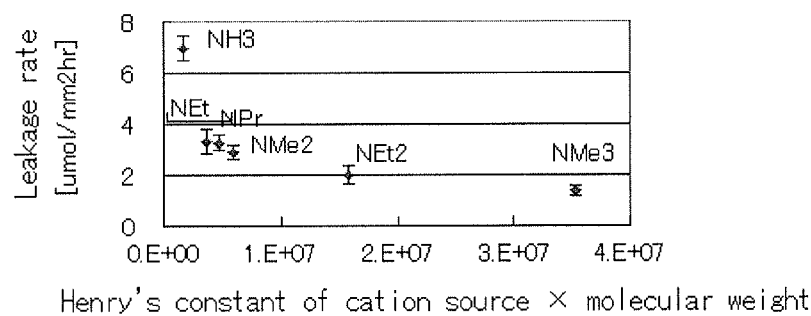
FIG. 4 is a graph showing the correlation between the Henry's law constant multiplied by the molecular weight and leakage.

Concentrations of 0.4 mol of ammonia (made by Kanto Chemical Co., Inc.), dimethyl amine (made by Tokyo Chemical Industry Co., Ltd.), ethyl amine (made by Tokyo Chemical Industry Co., Ltd.), propyl amine (made by Wako Pure Chemical Industries, Ltd.), trimethyl amine (made by Wako Pure Chemical Industries, Ltd.), and diethyl amine (made by Wako Pure Chemical Industries, Ltd.) per kilogram of pure water were prepared as draw solutions. Pure water was employed as the feed solution. An Expedition built-in membrane made by Hydration Technology Innovations (referred to as an "HT membrane" hereinafter) was employed as the semi-permeable membrane. A 100 mL quantity of feed solution and 100 mL of draw solution were pumped at a flow rate of 20 mm/second with a Peri-Star pump and the feed solution and draw solution were brought into contact through the semi-permeable membrane in a cell holding a semi-permeable membrane (HT membrane). At the time, the membrane contact surface area was 280 mm$^2$ and the two flows were parallel and identically oriented. The two solutions were contacted while being fed for 30 minutes, after which the concentration of each cation source in the feed solution was measured and the semi-permeable membrane permeation rate was estimated. The pH and electrical conductivity of the feed solutions were measured and the cation concentration of each cation source contained was estimated from a calibration curve. The results are given in Table 2. FIG. 3 shows the correlation with the molecular weight of the cation source and FIG. 4 shows the correlation with the value of the molecular weight multiplied by the Henry's law constant of the cation source.

TABLE 1

| | Solute (Uncharged state) | Henry's constant | Molecular weight | pKa or pKb | Boiling point [° C.] |
|---|---|---|---|---|---|
| Cation | Trimethylamine | 6.0E+05 | 60.11 | 4.21 | 3 |
| | Dimethyl ethyl amine | 4.0E+05 | 74.14 | 4.17 | 36 |
| | Isopropyl amine | 2.6E+05 | 60.11 | 3.37 | 33 |
| | Diethyl amine | 2.2E+05 | 74.14 | 2.98 | 55.5 |
| | Dimethyl amine | 1.3E+05 | 46.08 | 3.27 | 7 |
| | Ethyl amine | 8.0E+04 | 46.08 | 3.3 | 17 |
| | Propyl amine | 7.8E+04 | 60.11 | 3.33 | 48 |
| | Pentyl amine | 1.4E+05 | 88.16 | 3.4 | 104 |
| | Ammonia (comparing) | 9.8E+04 | 18.03 | 4.75 | −33 |
| | Ethylenediamine (comparing) | 9.7E+00 | 61.1 | 3.92 | 116 |
| Anion | $CO_2$ | 1.6E+08 | 44.01 | 6.35 | −79 |
| | $SO_2$ | 4.6E+06 | 64.07 | 1.81 | −10 |
| | Trifluoroacetic acid(comparing) | 7.7E+02 | 114.03 | 0.3 | 72 |

Rate of Leakage of Solute Through Semi-Permeable Membrane

The rate at which just the cation source permeated through the semi-permeable membrane from an aqueous solution was analyzed in a model experiment of the rate of leakage of the solute in the diluting means. Of the anion source and its charged materials and the cation source and its charged materials, the uncharged cation source was known to pass the most readily through a semi-permeable membrane when carbon dioxide was employed as the anion source in the present invention. Thus, the analysis was effective in that the cation source was selected.

TABLE 2

| | | | | | Rate of leakage | |
|---|---|---|---|---|---|---|
| Cation source | Abbreviation | Henry's constant [Pa/molfrac] | Molecular weight [g/mol] | Henry × MW [gPa/mol molfrac] | Average [umol/mm$^2$hr] | Standard deviation |
| Ammonia | $NH_3$ | 9.8E+04 | 17 | 1.66E+06 | 6.92 | 0.51 |
| Dimethyl amine | $NMe_2$ | 1.3E+05 | 45.08 | 5.86E+06 | 2.85 | 0.26 |
| Ethyl amine | NEt | 8.0E+04 | 45.08 | 3.59E+06 | 3.30 | 0.48 |
| Propyl amine | NPr | 7.8E+04 | 59.11 | 4.61E+06 | 3.21 | 0.31 |
| Trimethylamine | $NMe_3$ | 6.0E+05 | 59.11 | 3.53E+07 | 1.36 | 0.2 |
| Diethyl amine | $NEt_2$ | 2.2E+05 | 73.14 | 1.58E+07 | 1.96 | 0.34 |

As shown in Table 2 and FIG. 3, the results indicated that the use of a cation source with a molecular weight of 31 or greater suppressed the semi-permeable membrane permeation rate. As shown in FIG. 4, the selection of a cation source with a high Henry's law constant in addition to a high molecular weight better suppressed the semi-permeable membrane permeation rate.

Adjustment of Draw Solution

Draw solutions with the compositions shown in Table 3 were prepared. For $CO_2$, gas absorption was conducted with carbon dioxide (using a $CO_2$ gas cylinder) while cooling a cation source aqueous solution prepared in advance. Trifluoroacetic acid (made by Wako Pure Chemical Industries, Ltd.) was added in liquid form. For $SO_2$, a sulfurous acid aqueous solution (made by Wako Pure Chemical Industries, Ltd.) was employed in the preparation.

Adjustment of Feed Solution

A 0.1 weight % solution (0.1% BSA) of bovine serum albumin (made by Wako Pure Chemical Industries, Ltd.) or a 0.6 M solution (0.6M NaCl) of sodium chloride (made by Wako Pure Chemical Industries, Ltd.) was employed as the feed solution.

Figure 2:
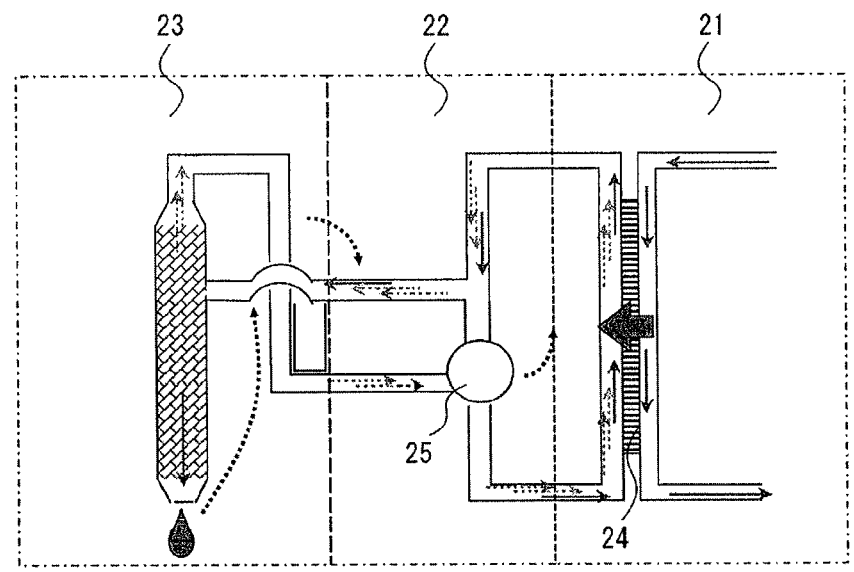
FIG. 2 is an example showing the configuration of the FO apparatus employed in an embodiment of the present application.

In the FO apparatus shown in FIG. 2, the diluting means and separating means were independently assembled. In FIG. 2, the solid line arrows indicate the flow of the feed solution or of water separated from the feed solution and the dotted lines indicate the flow of the draw solution or of the draw solution solute, respectively. The present FO apparatus is comprised of a diluting means 21, a dissolving means 22, and a separating means 23.

Initially, as a diluting means, 200 mL of feed solution and 200 mL of draw solution were brought into contact through a semi-permeable membrane 24 (HT membrane) in diluting means 21 (membrane contact surface area 280 mm$^2$). Each solution was pumped at a flow rate of 20 mm/second in parallel with the same orientation using a Peri-Star pump. The rate at which the water in the feed solution permeated to the dissolving means 22 side through semi-permeable membrane 24 was analyzed by measuring the weights of the feed solution and draw solution in real time. The cation concentration that had leaked out from the draw solution and was contained in the feed solution after flowing for three hours was quantified with various amine electrodes or by gas chromatography, and the leakage rate was computed. The amine electrodes employed in amine quantification were obtained by replacing the internal liquid of commercial ammonia electrodes (made by DKK-TOA Corporation, comprising ammonia composite electrodes AE-2041 connected to a portable ion meter IM-32P) with a chloride aqueous solution of the amine to be measured (for example, 50 mM trimethyl amine chloride aqueous solution). The measurement method consisted of adjusting the pH of the sample liquid with NaOH aqueous solution and then measuring the electromotive force in a stable state. Calibration curves of amine concentration and electromotive force were prepared for various aqueous solution concentrations of various measurement controls and the amine concentrations of the samples were then estimated.

Next, a stripping column was employed as a separating means to measure the amount of remaining solute. A dual-tube configuration stripping column with a built-in structured packing (Laboratory Packing EX, made by Sulzer Chemtech: referred to as "Labpack" hereinafter) was employed as the stripping column. While heating the bottom with a mantle heater, the draw solution that had been diluted by water from the feed solution was continuously fed from the top of the stripping column. In the stripping column of separating means 23, the solute component of the draw solution was volatilized to separate the water from the solute component of the draw solution. At the time, the top of the column was connected through a cooling element to a vacuum pump and the internal pressure was automatically regulated to $1.0 \times 10^1$ Pa. During three hours of operation, a suitable quantity of separated liquid was sampled from the bottom of the column and the concentration of cations remaining in the solution discharged from the bottom of the stripping column while in a steady state was measured. The measurement was conducted by the same method as in the above diluting means.

Permeation Flow Rate

The semi-permeable membrane permeation flow rate of water from the feed solution was measured in the above process.

○: 300 μmol/mm$^2$ hr or more
Δ: 30 μmol/mm$^2$ or more but less than 300 μmol/mm$^2$
X: less than 30 μmol/mm$^2$ Above, Δ or better indicates a practical level.

The Leakage Rate

The leakage of solute component through the semi-permeable membrane to the draw solution was measured in the above process. The following evaluation was conducted.

○: less than 1 μmol/mm$^2$
Δ: 1 μmol/mm$^2$ or more but less than 5 μmol/mm$^2$
X: more than 5 μmol/mm$^2$ Above, Δ or better indicates a practical level.

Amount of Remaining Solute

The amount of draw solution remaining in the water after separation of the cation source and anion source from the draw solution was measured. The following evaluation was conducted.

◎: less than 50 μM
○: 50μ or more but less than 200 μM
Δ: 200 μM or more but less than 1 mM
X: 1 mM or more Above, Δ or better indicates a practical level.

TABLE 3

| | Species (Uncharged state) | Content [mol/ kg H$_2$O] | Species (Uncharged state) | Content [mol/ kg H2O] | Feed solution | Flow rate | Leakage rate | Amount of remaining solute |
|---|---|---|---|---|---|---|---|---|
| Example 1 | Trimethylamine | 4.2 | CO$_2$ | 3 | 0.1% BSA | ○ | ○ | ◎ |
| Example 2 | Trimethylamine | 4.2 | CO$_2$ | 3 | 0.6M NaCl | ○ | ○ | ◎ |
| Example 3 | Dimethyl ethyl amine | 4.2 | CO$_2$ | 3 | 0.1% BSA | ○ | ○ | ◎ |
| Example 4 | Dimethyl ethyl amine | 4.2 | CO$_2$ | 3 | 0.6M NaCl | ○ | ○ | ◎ |
| Example 5 | Isopropyl amine | 4.2 | CO$_2$ | 3 | 0.1% BSA | ○ | ○ | ○ |
| Example 6 | Isopropyl amine | 4.2 | CO$_2$ | 3 | 0.6M NaCl | ○ | ○ | ○ |
| Example 7 | Diethyl amine | 4.2 | CO$_2$ | 3 | 0.6M NaCl | ○ | ○ | ○ |
| Example 8 | Propyl amine | 4.2 | CO$_2$ | 3 | 0.6M NaCl | ○ | Δ | ○ |
| Example 9 | Ethyl amine | 4.2 | CO$_2$ | 3 | 0.6M NaCl | ○ | Δ | ○ |

TABLE 3-continued

| | Species (Uncharged state) | Content [mol/kg H$_2$O] | Species (Uncharged state) | Content [mol/kg H2O] | Feed solution | Flow rate | Leakage rate | Amount of remaining solute |
|---|---|---|---|---|---|---|---|---|
| Example 10 | Pentyl amine | 4.2 | CO$_2$ | 3 | 0.6M NaCl | ○ | ○ | Δ |
| Example 11 | Trimethylamine | 1.4 | CO$_2$ | 1 | 0.1% BSA | Δ | ○ | ◎ |
| Example 12 | Trimethylamine | 1.4 | CO$_2$ | 1 | 0.6M NaCl | Δ | ○ | ◎ |
| Example 13 | Dimethyl ethyl amine | 1.4 | CO$_2$ | 1 | 0.1% BSA | Δ | ○ | ◎ |
| Example 14 | Trimethylamine | 4.2 | CO$_2$ | 2 | 0.6M NaCl | ○ | Δ | ◎ |
| Comparative Example 1 | Trimethylamine | 4.2 | — | — | 0.6M NaCl | X | X | ◎ |
| Comparative Example 2 | — | — | SO$_2$ | 0.5 | 0.1% BSA | Δ | ○ | X |
| Comparative Example 3 | Ammonia | 4.2 | CO$_2$ | 3 | 0.6M NaCl | ○ | X | ○ |
| Comparative Example 4 | Ammonia | 1.4 | CO$_2$ | 1 | 0.6M NaCl | Δ | X | ○ |
| Comparative Example 5 | Ethylenediamine | 4.2 | CO$_2$ | 3 | 0.1% BSA | ○ | Δ | X |
| Comparative Example 6 | Trimethylamine | 0.75 | Trifluoro acetic acid | 0.45 | 0.1% BSA | ○ | Δ | X |

As will be clear from the above table, when the cation source employed had a Henry constant of less than $1.0 \times 10^4$ (Pa/mol·fraction) or the molecular weight of the cation source was less than 31 (Comparative Examples 3 to 5), the leakage rate and quantity of remaining solute deteriorated. When the Henry's law constant of the anion source was less than $1.0 \times 10^4$ (Pa/mol·fraction) (Comparative Example 6), the quantity of remaining solute deteriorated.

When the molecular weight of the cation source in a uncharged state was 31 or greater and the Henry's law constant of each of the cation source and anion source in a standard state was $1.0 \times 10^4$ (Pa/mol·fraction) or greater, the permeation flow rate, leakage rate, and quantity of remaining solute were all good. When the Henry's law constant of each of the cation source and anion source was $1.00 \times 10^5$ (Pa/mol·fraction) or greater and the molecular weight of the cation source fell within a range of 45 to 74, these effects were found to be particularly good. When the Henry's law constant of each of the cation source and anion source was $3.00 \times 10^5$ (Pa/mol·fraction) or greater, these effects were found to be even better. When the pKb of the cation source fell within a range of 4.0 to 4.5, these effects were found to be still better. When trimethyl amine or dimethyl ethyl amine was employed as the cation source and carbon dioxide was employed as the anion source, these effects were found to be particularly good.

Figure 5:
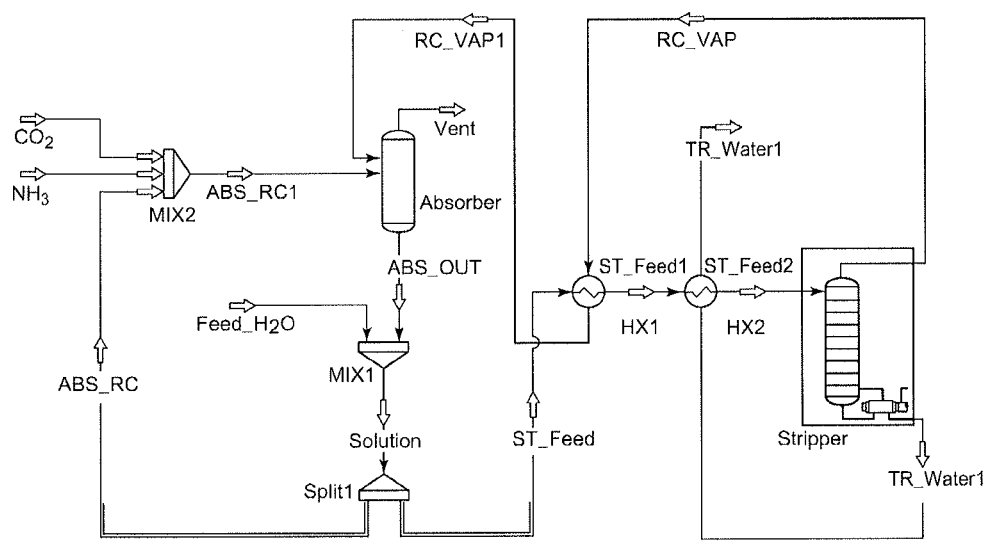
FIG. 5 is a simulation flow diagram employed in an embodiment of the present application.

Overall energy simulations were conducted for the FO apparatus shown in FIG. 2 for Embodiments 2, 6, and 7 and Comparative Example 3. FIG. 5 shows a schematic of the system employed in the simulation. Therein, Absorber denotes the dissolving means, Stripper denotes the separating means, and MIX1 denotes the diluting element. The cation source employed was ammonia or various amines, and the anion source was carbon dioxide. Data stored in OLI Systems were employed for the various physical properties of the cation sources and anion sources. In terms of scale, although not directly relating to the results, the flow rate of the water that could be purified (TR_WATER) was estimated at 1,000 tons/day.

The concentration of the cation source and anion source in the diluting element was diluted with 25° C. pure water from 4.2 mol and 3.0 mol per kilogram of water to 1.4 mol and 1.0 mol, respectively. There was considered to be no loss of cation solution or anion solution during this process. The diluted draw solution (Solution) was split at Stripper and Absorber by Split1. The split ratio at that time was about 2:1. However, the Stripper side was set high so that the targeted concentration would be achieved in the Absorber even when water migrated into the Absorber along with the cation source and anion source from the Stripper. A packed stripping column with 30 theoretical segments was employed as the Stripper and there was deemed to be no pressure loss. The pressure was set to a pressure (the saturation vapor pressure of the draw solution at 25° C.) such that the concentration of the cation source and anion source reached 4.2 mol and 3.0 mol per kilogram at an ultimate temperature of 25° C. when the Absorber contained in the TR_WATER was cooled. The temperature at the bottom of the stripper column was set so that at that pressure, the concentration of the cation source contained in water (TR_WATER) obtained from the bottom of the Stripper became 60 μmol per kilogram of water. In the simulation, the gas (vent) removed from the top of the Absorber was set. However, the level was so small relative to the whole as to be negligible. The diluted draw solution (ABS_RC) that was split at Split1 was considered to have been introduced into the Absorber following dissolution of the anion source and cation source at 25° C. in MIX2. The anion source and cation source were replenished at that time in quantities that made up for the losses due to retention in the TR_WATER.

As shown in FIG. 5, heat was exchanged by heat exchangers (HX1, HX2) in two spots. The UA values of the heat exchangers were set to $4.0 \times 10^8$ and $2.0 \times 10^9$, respectively. There was considered to be no heat loss through the piping, pressure loss, or precipitation of salt due to nonuniform states. There was considered to be no rate controlling of reaction rates such as the hydration reaction or the diffusion rate. Mixed phase flows of gases and liquids were considered to be suitable. Of the results obtained, the level of heating at the bottom of the Stripper was estimated to be the required energy.

Table 4 shows the simulation results. As indicated in Table 4, the required energy in Embodiments 6 and 7 and in Comparative Example 3 was 100 kWh/m$^3$ (the sum total of the thermal energy required for 1 m$^3$ of water) or higher. By contrast, this became 67 kWh/m$^3$ under conditions of concentrations of 4.2 mol/kg and 3.0 mol/kg, respectively, in the dissolving means when trimethyl amine was employed as the cation source and carbon dioxide was employed as the anion source in Embodiment 2. That indicated considerable energy conservation. This was primarily attributed to suppression of the quantity of needlessly volatilizing water in the Stripper.

TABLE 4

| | Draw solution | | | Stripping performance | |
| | Cation source | | Chanege anion source | | Level of heating of |
| | Species | Amount of change [mol/kg] | Species | Amount of change [mol/kg] | Stripper column [kWh/m$^3$] | Energy conservation |
|---|---|---|---|---|---|---|
| Example 2 | Trimethylamine | 4.2→1.4 | $CO_2$ | 3.0→1.0 | 67 | ◉ |
| Example 6 | Isopropyl amine | 4.2→1.4 | $CO_2$ | 3.0→1.0 | 215 | ○ |
| Example 7 | Diethyl amine | 4.2→1.4 | $CO_2$ | 3.0→1.0 | 362 | ○ |
| Comparative Example 3 | Ammonia | 4.2→1.4 | $CO_2$ | 3.0→1.0 | 117 | ○ |

Table 5 shows the Absorber temperature and Stripper column bottom temperature in the above simulation. As indicated in Table 5, in Comparative Example 3, the Stripper column bottom temperature, that is, the highest heating temperature, was 63° C. By contrast, in Embodiment 2, it was estimated to be 51° C., resulting in a temperature differential with the absorber temperature of 26° C. That was extremely low relative to the temperature differential of 38° C. of Comparative Example 3. The fact that the difference in the heating temperature and cooling temperature of the apparatus as a whole was small indicates in and of itself that the apparatus could be run with a low quality energy source. Thus, the results obtained for Embodiment 2 indicate extremely good economic efficiency.

TABLE 5

| | Cation source | Absorber temperature (Absorber) | Stripper column bottom temperature (Stripper) | Temperature differential | Energy conservation |
|---|---|---|---|---|---|
| Example 2 | Trimethylamine | 25° C. | 51° C. | 26° C. | ◉ |
| Comparative Example 3 | Ammonia | 25° C. | 63° C. | 38° C. | Δ |

KEY TO NUMBERS

11 Seawater
12 Draw solution
13 Semi-permeable membrane
14 Stripping column
15 Volatile component of draw solution
16 Water
17 Gas absorber
18 Pressure gauge
21 Diluting means
22 Dissolving means
23 Separating means
24 Semi-permeable membrane
25 Gas absorber

What is claimed is:

1. A forward osmosis process, comprising:
   bringing a feed solution and a draw solution comprising a dissolved cation source and an anion source into contact through a semi-permeable membrane and diluting the draw solution with a water separated from the feed solution by the semi-permeable membrane;
   separating the diluted draw solution into the cation source and anion source and into water; and
   returning the separated cation source and anion source to, and dissolving the separated cation source and anion source in, the diluted draw solution;
   wherein the cation source has a molecular weight of 31 or greater in an uncharged state, and each of the anion source and the cation source has a Henry's law constant of $1.0 \times 10^4$ (Pa/mol·fraction) or greater in water in a standard state.

2. The forward osmosis process according to claim 1, wherein the anion source has an acid dissociation constant (pKa) of 6.0 to 7.0 as an uncharged material in a standard state.

3. The forward osmosis process according to claim 1, wherein the cation source has a base dissociation constant (pKb) of 2.0 to 4.5 as an uncharged material in a standard state.

4. The forward osmosis process according to claim 1, wherein the cation source, and/or anion source, has a boiling point of less than 100° C. at 1 atm as an uncharged material.

5. The forward osmosis process according to claim 1, wherein the cation source has a base dissociation constant (pKb) of 4.0 to 4.5 as an uncharged material in a standard state.

6. The forward osmosis process according to claim 1, wherein the cation source has a Henry's law constant of $1.0 \times 10^5$ (Pa/mol·raction) or greater in water in a standard state.

7. The forward osmosis process according to claim 1, wherein the cation source has a Henry's law constant of $3.0 \times 10^5$ (Pa/mol·raction) or greater in water in a standard state.

8. The forward osmosis process according to claim 1, wherein each of the anion source and cation source in the draw solution has a concentration immediately prior to being contacted with the semi-permeable membrane of 2.4 mol or more per kilogram of water.

9. The forward osmosis process according to claim 1, wherein the anion source comprises anions selected from the group consisting of carbonate ions, hydrogen carbonate ions or a combination thereof.

10. The forward osmosis process according to claim 1, wherein the molar ratio of the anion source to cation source is from 1:1 to 1:2.

11. The forward osmosis process according to claim 1, wherein the cation source and anion source each have a Henry's law constant of $1.00 \times 10^5$ (Pa/mol·fraction) or greater in water in a standard state, and the cation source has a molecular weight within a range of from 45 to 74.

12. The forward osmosis process according to claim 1, wherein the diluted draw solution is separated into the cation source and anion source and into water by heating diluted draw solution to a temperature not exceeding 90° C.

13. The forward osmosis process according to claim 1, wherein in the step of bringing a feed solution and a draw solution into contact, the draw solution has a temperature of ±5° C. of the feed solution.

14. The forward osmosis process according to claim 1, wherein another part of diluted draw solution which is not introduced to the separating step is warmed in a heat exchanger which uses, as a heat source, at least one among the water, cation source, and anion source obtained in the separating step.

15. The forward osmosis process according to claim 1, wherein the difference between a maximum temperature of water obtained in the separating step and a minimum temperature of draw solution in the dissolving step is less than 35° C.

16. The forward osmosis process according to claim 1, wherein the forward osmosis process is a water purification process that separates the diluted draw solution into a cation source and anion source and into water, and recovers the water component as a target product.

17. The forward osmosis process according to claim 1, wherein the feed solution is seawater.

18. The forward osmosis process according to claim 1, wherein the forward osmosis process further comprises collecting a concentrated target product that is left over from the feed solution after bringing the feed solution and draw solution into contact through the semi-permeable membrane.

* * * * *